(12) United States Patent
Amari et al.

(10) Patent No.: US 11,523,670 B2
(45) Date of Patent: *Dec. 13, 2022

(54) METHOD FOR PRODUCING COATING FILM BY ELECTROSTATIC SPRAYING

(71) Applicant: Kao Corporation, Tokyo (JP)

(72) Inventors: Naomi Amari, Ichikai-machi (JP); Takehiko Tojo, Utsunomiya (JP); Motoaki Ito, Matsudo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,998

(22) PCT Filed: Oct. 17, 2016

(86) PCT No.: PCT/JP2016/080675
§ 371 (c)(1),
(2) Date: Apr. 17, 2018

(87) PCT Pub. No.: WO2017/069080
PCT Pub. Date: Apr. 27, 2017

(65) Prior Publication Data
US 2019/0059551 A1    Feb. 28, 2019

(30) Foreign Application Priority Data
Oct. 19, 2015  (JP) .............................. JP2015-205933

(51) Int. Cl.
| | |
|---|---|
| A61K 8/34 | (2006.01) |
| A61Q 1/02 | (2006.01) |
| A45D 34/04 | (2006.01) |
| A61Q 1/00 | (2006.01) |
| B05D 1/04 | (2006.01) |
| A61K 8/35 | (2006.01) |
| A61K 8/31 | (2006.01) |
| A61M 35/00 | (2006.01) |
| A61K 8/04 | (2006.01) |
| A61K 8/891 | (2006.01) |
| A61K 8/92 | (2006.01) |
| A61K 8/81 | (2006.01) |
| A61K 8/63 | (2006.01) |
| A61K 8/02 | (2006.01) |
| B05B 5/16 | (2006.01) |
| A61L 26/00 | (2006.01) |

(52) U.S. Cl.
CPC .............. *A45D 34/04* (2013.01); *A61K 8/027* (2013.01); *A61K 8/046* (2013.01); *A61K 8/31* (2013.01); *A61K 8/34* (2013.01); *A61K 8/345* (2013.01); *A61K 8/35* (2013.01); *A61K 8/63* (2013.01); *A61K 8/817* (2013.01); *A61K 8/8129* (2013.01); *A61K 8/891* (2013.01); *A61K 8/922* (2013.01); *A61M 35/00* (2013.01); *A61M 35/003* (2013.01); *A61Q 1/00* (2013.01); *A61Q 1/02* (2013.01); *B05B 5/1683* (2013.01); *B05B 5/1691* (2013.01); *B05D 1/04* (2013.01); *A61K 2800/412* (2013.01); *A61K 2800/805* (2013.01); *A61K 2800/87* (2013.01); *A61K 2800/884* (2013.01); *A61L 26/00* (2013.01)

(58) Field of Classification Search
None
See application file for complete search history.

(56) References Cited

U.S. PATENT DOCUMENTS

| | | | |
|---|---|---|---|
| 5,268,166 A | | 12/1993 | Barnett et al. |
| 6,252,129 B1 | * | 6/2001 | Coffee .............. A61F 13/00085 239/3 |
| 6,461,626 B1 | | 10/2002 | Rabe et al. |
| 6,514,504 B1 | | 2/2003 | Yen et al. |
| 6,531,142 B1 | | 3/2003 | Rabe et al. |

(Continued)

FOREIGN PATENT DOCUMENTS

| | | | |
|---|---|---|---|
| FR | 2819176 | * | 7/2002 |
| JP | 5-194145 A | | 8/1993 |

(Continued)

OTHER PUBLICATIONS

Extended European Search Report dated Apr. 18, 2019 in European Patent Application No. 16857395.4, 8 pages.

(Continued)

*Primary Examiner* — Tigabu Kassa
(74) *Attorney, Agent, or Firm* — Oblon, McClelland, Maier & Neustadt, L.L.P.

(57) ABSTRACT

The present invention relates to preventing color transfer and sticking of powder-containing cosmetics to clothes or the like. A coating formation method of the present invention includes an electrostatic spraying step of electrostatically spraying a composition directly onto a skin surface onto which powder-containing cosmetics have been applied, thereby forming a coating on the skin. The composition contains a component (a) and a component (b) below. It is preferable that the method further includes a liquid agent applying step of applying a liquid agent containing one or more selected from water and oils that are in liquid form at 20° C. on the skin onto which the powder-containing cosmetics have been applied, wherein the liquid agent applying step is performed subsequent to the electrostatic spraying step. (a) One or more volatile substances selected from water, alcohols, and ketones; and (b) a polymer having a coating formation ability.

8 Claims, 1 Drawing Sheet

(56) References Cited

U.S. PATENT DOCUMENTS

| | | | |
|---|---|---|---|
| 7,823,809 B2 * | 11/2010 | Yamaguchi | B05B 5/005 128/200.14 |
| 2001/0003148 A1 | 6/2001 | Coffee | |
| 2002/0155069 A1 | 10/2002 | Pruche et al. | |
| 2002/0192252 A1 | 12/2002 | Yen et al. | |
| 2003/0059599 A1 | 3/2003 | Beckley et al. | |
| 2004/0076649 A1 * | 4/2004 | Blin | A61K 8/02 424/401 |
| 2006/0235351 A1 | 10/2006 | Matsumura et al. | |
| 2007/0060666 A1 * | 3/2007 | Taniguchi | B65B 3/326 523/105 |
| 2008/0119772 A1 | 5/2008 | Coffee | |
| 2010/0112019 A1 * | 5/2010 | Thevenet | A61Q 1/02 424/401 |
| 2010/0224209 A1 | 9/2010 | Rabe et al. | |
| 2010/0224210 A1 | 9/2010 | Rabe et al. | |
| 2010/0224211 A1 | 9/2010 | Rabe et al. | |
| 2010/0286591 A1 | 11/2010 | Coffee | |
| 2013/0058880 A1 * | 3/2013 | Dong | C08K 5/5419 424/63 |

FOREIGN PATENT DOCUMENTS

| | | |
|---|---|---|
| JP | 2003-506470 A | 2/2003 |
| JP | 2003-506474 A | 2/2003 |
| JP | 2003-507166 A | 2/2003 |
| JP | 2004-501177 A | 1/2004 |
| JP | 2006-95332 A | 4/2006 |
| JP | 2006-104211 A | 4/2006 |
| JP | 2006-296511 A | 11/2006 |
| JP | 4077035 B2 | 4/2008 |
| JP | 4130678 B2 | 8/2008 |
| JP | 2010-270334 A | 12/2010 |
| JP | 2012-515062 A | 7/2012 |
| WO | WO 01/12139 A1 | 2/2001 |
| WO | WO 01/12335 A1 | 2/2001 |
| WO | WO 01/26610 * | 4/2001 |

OTHER PUBLICATIONS

Database GNPD Mintei, "Treatment Clear Base", Retrieved from the internet: www.gnpd.com, Apr. 2013, XP055578649, 5 pages.

Database GNPD Mintei. "Makeup Setting Spray", Retrieved from the internet: www.gnpd.com. Aug. 2015, XP055578800. 3 pages.

International Search Report dated Dec. 20, 2016 in PCT/JP2016/080675 filed Oct. 17, 2016.

* cited by examiner

METHOD FOR PRODUCING COATING FILM BY ELECTROSTATIC SPRAYING

TECHNICAL FIELD

The present invention relates to a method for forming a coating on skin onto which powder-containing cosmetics have been applied.

BACKGROUND ART

Various methods for forming a coating by electrostatic spraying are known. For example, Patent Literature 1 describes a method for treating skin, the method including electrostatically spraying a composition on the skin. The composition used in this method includes an electrically insulating liquid material, a conductive substance, a particulate powder material, and a thickener. Cosmetics that contain a pigment, and compositions for skin care are typically used as this composition. Specifically, cosmetic foundation is used as this composition. That is, the invention described in Patent Literature 1 is intended to be mainly used to electrostatically spray the cosmetic foundation and apply the cosmetic foundation on the skin for the purpose of beauty treatment.

Patent Literature 2 describes a disposable cartridge to be used in an electrostatic spraying apparatus for cosmetics. This electrostatic spraying apparatus is a hand-held and self-contained type. This electrostatic spraying apparatus is used to spray cosmetic foundation as in Patent Literature 1 above.

CITATION LIST

Patent Literature

Patent Literature 1: US6,531,142B1
Patent Literature 2: WO01/12335A1

SUMMARY OF INVENTION

When skin onto which cosmetics such as foundation have been applied is brought into contact with clothes or the like and friction occurs therebetween, color transfer of the foundation or the like to the clothes often occurs. The same is applied to coatings of foundation formed through electrostatic spraying according to the methods described in Patent Documents 1 and 2. In particular, when a coating of foundation is formed according to the methods described in these documents, the adhesion between the skin and the coating is insufficient, and thus color transfer of the foundation to clothes or the like is more likely to occur.

The present invention provides a coating formation method including an electrostatic spraying step of electrostatically spraying a composition directly onto a skin surface onto which powder-containing cosmetics have been applied, thereby forming a coating on the skin.

The composition contains a component (a) and a component (b) below:
(a) one or more volatile substances selected from water, alcohols, and ketones; and
(b) a polymer having a coating formation ability.

DESCRIPTION OF EMBODIMENTS

The present invention relates to suppressing color transfer and sticking, to clothes or the like, of powder-containing cosmetics such as foundation applied onto skin, and keeping the powder-containing cosmetics on the skin.

Hereinafter, the present invention will be described based on a preferred embodiment thereof with reference to the drawings. In the present invention, a coating is formed by applying a composition containing predetermined components directly on a region onto which powder-containing cosmetics have been applied (hereinafter, this region is also referred to as a "cosmetics application region"), on the skin onto which the cosmetics have been applied. In other words, the cosmetics are protected by covering the surface of the cosmetics by applying a so-called top-coating onto the cosmetics application region. Accordingly, even when friction occurs between the cosmetics application region and clothes or the like, color transfer and sticking of the cosmetics to clothes or the like are effectively prevented. On the other hand, the techniques disclosed in Patent Documents 1 and 2 described in Background Art merely disclose that coatings of foundation are formed directly onto a skin surface using electrostatic spraying methods, and provide no means for protecting the formed coatings of foundation.

In the present invention, it is preferable that a coating is formed spanning the entire cosmetics application region, from the viewpoint of reliably preventing color transfer and sticking of cosmetics to objects such as clothes or the like in contact with skin, and of keeping the cosmetics on the skin. However, according to the circumstances, the coating may be formed only on part of the cosmetics application region. Alternatively, the coating may be formed so as to span over the cosmetics application region and regions onto which cosmetics are not applied.

In this specification, examples of "powder-containing cosmetics (may simply be referred to as the cosmetics in the present invention, hereinafter)" include external agents that provide skin with preferable effects, such as make-up cosmetics, UV cosmetics, and liquid cosmetics. Examples of the make-up cosmetics include base-make up cosmetics, lip cosmetics, cosmetic foundation, BB creams, and CC creams. Examples of the base-make up cosmetics include foundation, concealers, and face powders. The base-make up cosmetics contain powders such as a coloring pigment or an extender pigment, and whether their form is a liquid, a gel, an emulsion, or a solid for example makes no substantial difference.

In the present invention, the content of the powders in the powder-containing cosmetics varies according to the purpose, but is preferably 0.1 mass % or greater, and is preferably 100 mass % or less, and more preferably 95 mass % or less, from the viewpoint of improving the adhesion between the coating formed using the electrostatic spraying method and the skin. Furthermore, in the present invention, the powder is preferably a coloring pigment or a pearl pigment from the viewpoint of providing the skin with preferable effects found in make-up cosmetics, UV cosmetics, liquid cosmetics, or the like. In the present invention, the coloring pigment refers to a colored pigment and a white pigment. From similar viewpoints, the coloring pigment has an average particle size of preferably 0.1 μm or greater, and more preferably more than 0.1 μm, and of preferably 20 μm or less, and more preferably 15 μm or less. Note that the average particle size is a number average particle size as measured by a laser diffraction/scattering particle size distribution analyzer LA-910 (manufactured by Horiba, Ltd.).

There is no limitation on the coloring pigment and the extender pigment contained in the base-make up cosmetics, as long as they are used in common cosmetics. Examples thereof include: inorganic powders such as silicic acid, silicic anhydride, magnesium silicate, talc, sericite, mica, kaolin, red iron oxide, clay, bentonite, mica, titanium coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof; organic powders such as polyamide, nylon, polyester, polypropylene, polystyrene, polyurethane, vinyl resin, urea resin, phenol resin, fluoropolymer resin, silicone resin, acrylic resin, melamine resin, epoxy resin, polycarbonate resin, divinylbenzene-styrene copolymer, silk powder, cellulose, long-chain alkyl phosphoric acid metal salt, N-mono long-chain alkylacyl basic amino acid, and composites thereof; and composite powders of the inorganic powders and the organic powders. These extender pigments and coloring pigments are colored or non-colored (e.g., white or substantially transparent), and can provide the composition or the skin with one or more effects from among coloring, light diffraction, oil absorption, translucency, opacity, glossiness, a matte appearance, smoothness, and the like.

Also, there is no limitation on the coloring pigment and the extender pigment contained in the cosmetics in the present invention, as long as they are used in common cosmetics. Examples thereof include: inorganic powders such as silicic acid, silicic anhydride, magnesium silicate, talc, sericite, mica, kaolin, red iron oxide, clay, bentonite, mica, titanium coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof; organic powders such as polyamide, nylon, polyester, polypropylene, polystyrene, polyurethane, vinyl resin, urea resin, phenol resin, fluoropolymer resin, silicone resin, acrylic resin, melamine resin, epoxy resin, polycarbonate resin, divinylbenzene-styrene copolymer, silk powder, cellulose, long-chain alkyl phosphoric acid metal salt, N-mono long-chain alkylacyl basic amino acid, and composites thereof; and composite powders of the inorganic powders and the organic powders. These extender pigments and coloring pigments are colored or non-colored (e.g., white or substantially transparent), and can provide the composition or the skin with one or more effects from among coloring, light diffraction, oil absorption, translucency, opacity, glossiness, a matte appearance, smoothness, and the like.

From the viewpoint of effectively preventing sticking to clothes, the cosmetics preferably contain a coloring pigment or a pearl pigment, and examples of the coloring pigment include: inorganic pigments such as titanium oxide, zinc oxide, yellow iron oxide, red iron oxide, black iron oxide, carbon black, ultramarine, indigo, indigo titanium oxide, black titanium oxide, chromium oxide, chromium hydroxide, and titanium-titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and organic pigments coated with macromolecules such as polymethacrylic acid ester. Furthermore, examples of the pearl pigment include titanated mica, red iron oxide coated mica, bismuth oxychloride, titanium oxide coated bismuth oxychloride, iron oxide coated titanated mica, organic pigment coated titanated mica, silicic acid-titanium treated mica, titanium oxide coated talc, silicon dioxide-red iron oxide treated aluminum, titanium oxide coated glass powder and other inorganic powders, flaky aluminum whose surface is coated with organic resins such as polyethylene terephthalate, and the like. Note that these coloring pigments, extender pigments, and pearl pigments may be used in a form that is surface-treated with fluorine compounds and silicone compounds, from the viewpoint of staying power against sweat and sebum.

Furthermore, from the viewpoint of effectively preventing sticking to clothes, the cosmetics preferably contain a coloring pigment or a pearl pigment, and examples of the coloring pigment include: inorganic white pigments such as titanium oxide, and zinc oxide; inorganic colored pigments such as yellow iron oxide, red iron oxide, black iron oxide, carbon black, ultramarine, indigo, indigo titanium oxide, black titanium oxide, chromium oxide, chromium hydroxide, and titanium-titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and organic pigments coated with macromolecules such as polymethacrylic acid ester. Furthermore, examples of the pearl pigment include inorganic powders such as titanated mica, red iron oxide coated (titanium oxide-aluminum hydroxide) mixture, red iron oxide coated mica, bismuth oxychloride, titanium oxide coated bismuth oxychloride, iron oxide coated titanated mica, organic pigment coated titanated mica, silicic acid-titanium treated mica, titanium oxide coated talc, silicon dioxide-red iron oxide treated aluminum, and titanium oxide coated glass powder; and the powders whose surface is coated with organic resins such as flaky aluminum coated with polyethylene terephthalate, and titanium oxide-yellow iron oxide-red iron oxide/lauryl methacrylate-dimethacrylic acid EG copolymer mixture, and the like.

Of these, if at least titanium oxide, yellow iron oxide, red iron oxide, or black iron oxide is contained as the coloring pigment, it is possible to achieve excellent make-up effects and effectively prevent sticking to clothes. Note that these coloring pigments and pearl pigments may be used in a hydrophobized form, from the viewpoint of staying power against sweat and sebum. The hydrophobization is preferably a surface treatment such as fluorine compound treatment, silicone compound treatment, alkyl treatment, alkylsilane treatment, metal soap treatment, water-soluble macromolecule treatment, amino acid treatment, N-acylamino acid treatment, lecithin treatment, organic titanate treatment, polyol treatment, acrylic resin treatment, methacrylic resin treatment, or urethane resin treatment, and more preferably a surface treatment with fluorine compounds or silicone compounds.

The coloring pigments and the pearl pigments may be used alone or in a combination of two or more, and, from the viewpoint of effectively preventing sticking to clothes, the content is preferably 0.1 mass % or greater, more preferably 0.5 mass % or greater, and even more preferably 1 mass % or greater, and is preferably 40 mass % or less, more preferably 30 mass % or less, and even more preferably 25 mass % or less, of the entire composition. Furthermore, the coloring pigments and the pearl pigments are contained in an amount of preferably 0.1 to 40 mass %, more preferably 0.5 to 30 mass %, and even more preferably 1 to 25 mass %, of the entire composition.

Furthermore, the make-up cosmetics may contain, in addition to the powders such as coloring pigments and extender pigments, an oil that is in liquid form at 25° C., a wax that is in solid form at 25° C., and the like. Moreover, the make-up cosmetics may contain as appropriate commonly used components such as thickeners, coating agents, surfactants, glucoses, polyhydric alcohols, water-soluble macromolecules, metal ion-sequestering agents, lower alcohols, amino acids, organic amines, pH control agents, skin conditioning agents, vitamins, antioxidants, flavoring substances, antiseptics, and the like, within a range where the effects of the present invention are not impaired.

The UV cosmetics preferably contain components having an ultraviolet light protection ability, such as an ultraviolet absorber or an ultraviolet light scattering agent. The ultraviolet absorber is preferably one or more organic ultraviolet absorbers selected from, for example, benzophenone derivatives such as dihydroxybenzophenone, dihydroxydimethoxybenzophenone, hydroxymethoxybenzophenone sulfonate, dihydroxydimethoxybenzophenone disulfonate, and methoxycinnamate derivatives such as 2-ethylhexyl methoxycinnamate, and more preferably 2-ethylhexyl methoxycinnamate. Examples of the ultraviolet light scattering agent include zinc oxide, titanium oxide, and silica composed of fine particles having an average particle size of 0.1 μm or less. Note that, prior to or subsequent to application of the cosmetics in the present invention onto the skin, for example, cosmetics other than the cosmetics of the present invention may be applied onto the skin.

In the present invention, an electrostatic spraying method is used as a method for forming a coating on the cosmetics application region. The electrostatic spraying method is a method in which a positive or negative high voltage is applied to a composition to electrify the composition, and then the electrified composition is sprayed toward a spray target. The sprayed composition spreads in a space while being repeatedly micronized due to Coulomb repulsion, and during this process or after the composition has attached to the spray target, a solvent, which is a volatile substance, dries to form a coating on the surface of the spray target.

The composition used in the electrostatic spraying method of the present invention (this composition is also referred to as "spray composition" hereinafter) is in liquid form in an environment where the electrostatic spraying method is performed. This composition contains a component (a) and a component (b) below:

(a) one or more volatile substances selected from a group consisting of water, alcohols, and ketones; and (b) a polymer having a coating formation ability.

Hereinafter, each composition will be described.

A volatile substance to be used as the component (a) is a substance having volatility in a liquid form. The component (a) is blended into the spray composition for the purpose of forming a dry coating in the following manner: when the spray composition, which has been placed in an electric field and sufficiently electrified, is discharged toward skin from the tip of a nozzle, the charge density of the spray composition becomes excessive as the component (a) evaporates, and then the component (a) further evaporates while the spray composition is further micronized due to Coulomb repulsion. For this purpose, the vapor pressure of the volatile substance at 20° C. is preferably 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.

Preferable examples of alcohols serving as the volatile substance to be used as the component (a) include chain aliphatic monohydric alcohols, cyclic aliphatic monohydric alcohols, and aromatic monohydric alcohols. Specific examples thereof include ethanol, isopropyl alcohol, butyl alcohol, phenylethyl alcohol, propanol, and pentanol. One or more alcohols selected from these alcohols can be used.

Examples of ketones serving as the volatile substance to be used as the component (a) include acetone, methyl ethyl ketone, and methyl isobutyl ketone. These ketones can be used alone or in combination of two or more.

The volatile substance to be used as the component (a) is more preferably at least one member selected from ethanol, isopropyl alcohol, butyl alcohol and water, even more preferably at least one member selected from ethanol and butyl alcohol, and even more preferably ethanol.

The spray composition contains, along with the component (a), a polymer having a coating formation ability to be used as the component (b). The polymer having a coating formation ability to be used as the component (b) is commonly a substance that can be dissolved in the volatile substance to be used as the component (a). The term "dissolve" as used herein refers to a state in which a substance is in a dispersed state at 20° C. and the dispersion is uniform when visually observed, and preferably transparent or translucent when visually observed.

As the polymer having a coating formation ability, a polymer is used that is appropriate according to the properties of the volatile substance to be used as the component (a). Specifically, polymers having a coating formation ability are roughly classified into water-soluble polymers and water-insoluble polymers. The term "water-soluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, 0.5 g or more of the immersed polymer dissolves in the water. On the other hand, the term "water-insoluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water.

Examples of the water-soluble polymers having a coating formation ability include naturally-occurring macromolecules such as pullulan, hyaluronic acid, chondroitin sulfate, poly-γ-glutamic acid, modified corn starch, β-glucan, glucooligosaccharide, mucopolysaccharide such as heparin and keratosulfate, cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, hydroxypropyl methyl cellulose; and synthetic macromolecules such as partially saponified polyvinyl alcohol (when not used in combination with a cross-linking agent), low saponified polyvinyl alcohol, polyvinyl pyrrolidone (PVP), polyethylene oxide, and sodium polyacrylate. These water-soluble polymers can be used alone or in combination of two or more. It is preferable to use pullulan and the synthetic macromolecules such as partially saponified polyvinyl alcohol, low saponified polyvinyl alcohol, polyvinyl pyrrolidone, and polyethylene oxide, of these water-soluble polymers, from the viewpoint of easily manufacturing the coating. When polyethylene oxide is used as the water-soluble polymer, its number average molecular weight is preferably 50,000 or more and 3,000,000 or less, and more preferably 100,000 or more and 2,500,000 or less.

On the other hand, examples of the water-insoluble polymers having a coating formation ability include completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethylsiloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin. These water-insoluble polymers can be used alone or in combination of two or more. It is preferable to use completely saponified polyvinyl alcohol, which can be insolubilized after the formation of a coating, partially saponified polyvinyl alcohol, which can be cross-linked after the formation of the coating when used in combination with a cross-linking agent, a polyvinyl butyral resin, oxazoline modified silicone such as a poly(N-propanoylethyleneimine)-grafted dimethylsiloxane/γ-aminopropylmethylsiloxane copolymer, water-soluble polyester, zein, and the like, of these water-insoluble polymers.

The content of the component (a) in the spray composition is preferably 50 mass % or more, more preferably 55 mass % or more, and even more preferably 60 mass % or more. In addition, the content of the component (a) in the spray composition is preferably 98 mass % or less, more preferably 96 mass % or less, and even more preferably 94 mass % or less. The content of the component (a) in the spray composition is preferably 50 mass % or more and 98 mass % or less, more preferably 55 mass % or more and 96 mass % or less, and even more preferably 60 mass % or more and 94 mass % or less. When the component (a) is blended into the spray composition in this proportion, the spray composition can sufficiently volatilize when the electrostatic spraying method is performed.

On the other hand, the content of the component (b) in the spray composition is preferably 2 mass % or more, more preferably 4 mass % or more, and even more preferably 6 mass % or more. In addition, the content of the component (b) in the spray composition is preferably 50 mass % or less, more preferably 45 mass % or less, and even more preferably 40 mass % or less. The content of the component (b) in the spray composition is preferably 2 mass % or more and 50 mass % or less, more preferably 4 mass % or more and 45 mass % or less, and even more preferably 6 mass % or more and 40 mass % or less. When the component (b) is blended into the spray composition in this proportion, a desired coating can be successfully formed.

The spray composition may include only the above-described component (a) and component (b) or may include other components in addition to the component (a) and the component (b). Examples of the other components include a plasticizer for the polymer having a coating formation ability to be used as the component (b), a coloring pigment, an extender pigment, a dye, a surfactant, a UV protection agent, a flavoring agent, a repellent, an antioxidant, a stabilizer, an antiseptic, and various vitamins. When the spray composition includes the other components, the blend proportion of the other components is preferably 0.1 mass % or more and 30 mass % or less, and more preferably 0.5 mass % or more and 20 mass % or less.

When the electrostatic spraying method is performed, the viscosity of the spray composition used in this method is preferably 1 mPa·s or more, more preferably 10 mPa·s or more, and even more preferably 50 mPa·s or more, at 25° C. In addition, the viscosity of the spray composition is preferably 5,000 mPa·s or less, more preferably 2,000 mPa·s or less, and even more preferably 1,500 mPa·s or less, at 25° C. The viscosity of the spray composition is preferably 1 mPa·s or more and 5,000 mPa·s or less, more preferably 10 mPa·s or more and 2,000 mPa·s or less, and even more preferably 50 mPa·s or more and 1,500 mPa·s or less, at 25° C. When the spray composition having a viscosity in this range is used, a porous coating, particularly a porous coating including a deposit of fibers, can be successfully formed with the electrostatic spraying method. The formation of the porous coating is advantageous from the viewpoint of preventing skin from getting sweaty. The viscosity of the spray composition is measured at 25° C. with an E-type viscometer. An E-type viscometer manufactured by Tokyo Keiki Inc. can be used as the E-type viscometer, for example. In this case, a rotor No. 43 can be used as a rotor.

Figure 1:
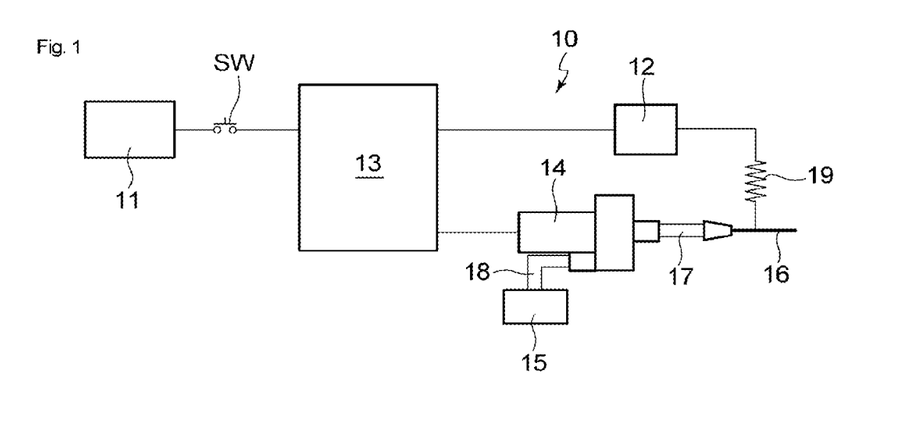
FIG. 1 is a schematic diagram illustrating a configuration of an electrostatic spraying apparatus to be preferably used in the present invention.

The spray composition is sprayed directly on human skin, which is a spray object, in the electrostatic spraying method. The electrostatic spraying method includes a step of electrostatically spraying the spray composition on the skin using an electrostatic spraying apparatus. FIG. 1 is a schematic diagram illustrating a configuration of an electrostatic spraying apparatus to be preferably used in the present invention. An electrostatic spraying apparatus 10 shown in this diagram includes a low-voltage power source 11. The low-voltage power source 11 can generate a voltage of several volts to a dozen or so volts. It is preferable that the low-voltage power source 11 is constituted by one or more batteries for the purpose of enhancing the portability of the electrostatic spraying apparatus 10. Also, when a battery is used as the low-voltage power source 11, there is an advantage in that the battery can be easily replaced as necessary. An AC adapter or the like can be used as the low-voltage power source 11 instead of the battery.

The electrostatic spraying apparatus 10 also includes a high-voltage power source 12. The high-voltage power source 12 is connected to the low-voltage power source 11 and includes an electric circuit (not shown) that boosts a voltage generated by the low-voltage power source 11 to a high voltage. A voltage boosting electric circuit usually includes a transformer, a capacitor, a semiconductor element, and the like.

The electrostatic spraying apparatus 10 further includes an auxiliary electric circuit 13. The auxiliary electric circuit 13 intervenes between the above-described low-voltage power source 11 and high-voltage power source 12 and has a function of adjusting the voltage of the low-voltage power source 11 to allow the high-voltage power source 12 to stably operate. Furthermore, the auxiliary electric circuit 13 has a function of controlling the rotation rate of a motor provided in a micro gear pump 14, which will be described later. The amount of the spray composition supplied from a container 15 for the spray composition, which will be described later, to the micro gear pump 14 is controlled by controlling the rotation rate of the motor. A switch SW is installed between the auxiliary electric circuit 13 and the low-voltage power source 11, and the operation of the electrostatic spraying apparatus 10 can be started/stopped by turning on/off the switch SW.

The electrostatic spraying apparatus 10 further includes a nozzle 16. The nozzle 16 is made of a conductor including various conductors typified by metal or a non-conductor such as plastic, rubber, or ceramic and has a shape allowing the spray composition to be discharged from the tip of the nozzle. A minute space through which the spray composition flows and that extends in the longitudinal direction of the nozzle 16 is formed inside the nozzle 16. With regard to the size of the cross section of this minute space, the diameter thereof is preferably 100 μm or more and 1,000 μm or less. The nozzle 16 is in communication with the micro gear pump 14 via a duct 17. The duct 17 may be made of a conductor or a non-conductor. The nozzle 16 is electrically connected to the high-voltage power source 12. This makes it possible to apply a high voltage to the nozzle 16. In this case, in order to prevent a case where excessive current flows when a human body is in direct contact with the nozzle 16, the nozzle 16 is electrically connected to the high-voltage power source 12 via a current limiting resistor 19.

The micro gear pump 14, which is in communication with the nozzle 16 via the duct 17, functions as a supply device for supplying the spray composition accommodated in the container 15 to the nozzle 16. The low-voltage power source 11 supplies power to the micro gear pump 14, so that the micro gear pump 14 operates. The micro gear pump 14 is configured to supply a predetermined amount of the spray composition to the nozzle 16 under the control of the auxiliary electric circuit 13.

The container 15 is connected to the micro gear pump 14 via a flexible duct 18. The spray composition is accommodated in the container 15. It is preferable that the container 15 is an exchangeable cartridge-type.

Figure 2:
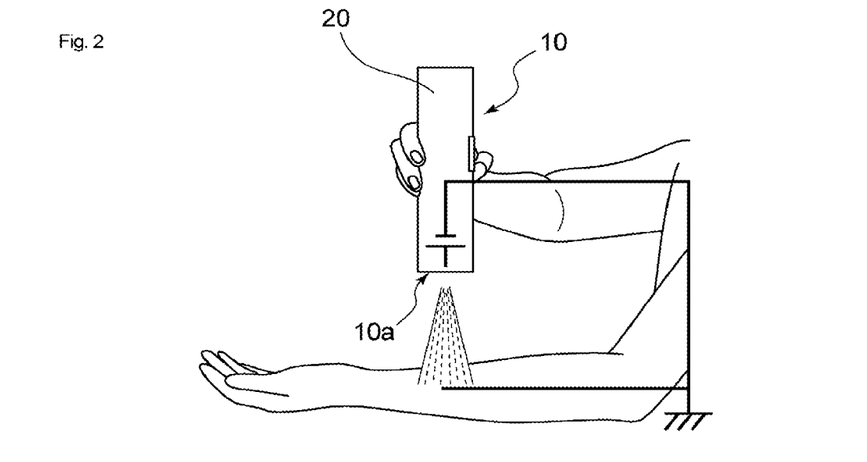
FIG. 2 is a schematic diagram illustrating a state in which an electrostatic spraying apparatus is used to perform an electrostatic spraying method.

The electrostatic spraying apparatus 10 configured as described above can be used as shown in FIG. 2, for example. FIG. 2 shows the hand-held electrostatic spraying apparatus 10 having dimensions allowing the apparatus to be held by one hand. In the electrostatic spraying apparatus 10 shown in this diagram, all of the members shown in the configuration diagram in FIG. 1 are accommodated in a cylindrical housing 20. The nozzle (not shown) is arranged at one end 10a in the longitudinal direction of the housing 20. The nozzle is arranged in the housing 20 in such a manner that the direction in which the composition is discharged matches the longitudinal direction of the housing 20 and the nozzle projects toward the skin. Since the tip of the nozzle is arranged so as to project toward the skin in the longitudinal direction of the housing 20, the spray composition is less likely to adhere to the housing, and the coating can be stably formed.

When the electrostatic spraying apparatus 10 is operated, a user, that is, a person who forms a coating on his/her cosmetics application region through electrostatic spraying, holds the apparatus 10 in their hand and directs the one end 10a of the apparatus 10 at which the nozzle (not shown) is arranged toward a cosmetics application region to be subjected to electrostatic spraying. FIG. 2 shows a state in which the one end 10a of the electrostatic spraying apparatus 10 is directed to the inner side of the forearm of the user. Under these conditions, the apparatus 10 is switched on to perform the electrostatic spraying method. When the apparatus 10 is turned on, an electric field is generated between the nozzle and the skin. In the embodiment shown in FIG. 2, a high positive voltage is applied to the nozzle, and the skin serves as a negative electrode. When the electric field is generated between the nozzle and the skin, the spray composition at the tip of the nozzle is polarized by electrostatic induction, thus shaping the tip of the spray composition into a cone shape. Then, electrified droplets of the spray composition at the tip of the nozzle are discharged into the air from the tip of the cone toward the skin along the electric field. When the component (a) used as a solvent evaporates from the electrified spray composition, which has been discharged into the air, the charge density of the surface of the spray composition becomes excessive, and the spray composition spreads in the space while being repeatedly micronized due to Coulomb repulsion and then reaches the skin. In this case, by appropriately adjusting the viscosity of the spray composition, it is possible to cause the sprayed composition to reach the cosmetics application region in the state in which the composition is in a droplet form. Alternatively, while the composition is being discharged into the space, it is also possible to evaporate the volatile substance used as a solvent from the droplets, solidify the polymer having a coating formation ability used as a solute to form fibers while the fibers are stretched and deformed due to an electric potential difference, and deposit the fibers onto the cosmetics application region. When the viscosity of the spray composition is increased, for example, it is easy to deposit the composition in a fibrous form onto the cosmetics application region. Accordingly, a porous coating composed of a deposit of fibers is formed on the surface of the cosmetics application region. The porous coating composed of a deposit of fibers can also be formed by adjusting the distance between the nozzle and the skin, and the voltage applied to the nozzle.

A high electric potential difference is generated between the nozzle and the skin while the electrostatic spraying method is being performed. However, an impedance is very large, and therefore, a current flowing in a human body is extremely small. The inventors of the present invention confirmed that a current flowing in a human body while the electrostatic spraying method is being performed is smaller by several digits than a current flowing in a human body due to static electricity generated in normal life, for example.

When the deposit of fibers is formed with the electrostatic spraying method, the thickness of the fibers expressed as a diameter of a corresponding circle is preferably 10 nm or more, and more preferably 50 nm or more. In addition, the thickness is preferably 3,000 nm or less, and more preferably 1,000 nm or less. The thickness of the fibers can be measured by observing the fibers magnified 10,000 times using a scanning electron microscopy (SEM), for example, removing defects (mass of fibers, intersection of fibers, and droplets) from the two-dimensional images of the fibers, selecting any ten fibers, drawing a line orthogonal to the longitudinal direction of each of the fibers, and reading the diameter of the fiber directly.

Although the above-mentioned fiber is a continuous fiber having an infinite length in the formation principle, it is preferable that the fiber has a length at least 100 times longer than its thickness. In this specification, a fiber having a length over 100 times than its thickness is defined as a "continuous fiber". It is preferable that a coating formed with the electrostatic spraying method is a porous discontinuous coating including the deposit of continuous fibers. The coating in such a form can be treated as one sheet including an aggregate and is characterized by being very soft, and therefore, there is an advantage in that the coating is unlikely to fall apart even when a shearing force is applied to the coating, and the coating has a good property of following to body movement. Also, there is an advantage in that the coating has a good property of diffusing sweat from the skin. Furthermore, there is an advantage in that the coating is easy to take off. In contrast, a continuous coating having no pores is not easy to take off and has a very low property of diffusing sweat. Therefore, the skin is likely to get sweaty.

The fibrous spray composition reaches the cosmetics application region in a state in which the composition is electrified. Since the skin is also electrified as described above, the fibers come into intimate contact with the cosmetics application region due to an electrostatic force. Since the skin surface is slightly uneven due to skin texture or the like, an anchor effect is obtained due to the unevenness, and the fibers thus come into further intimate contact with the surface of the cosmetics application region. After the electrostatic spraying is finished in this manner, the electrostatic spraying apparatus 10 is turned off. Accordingly, the electric field between the nozzle and the skin vanishes, and the electric charge on the skin surface is fixed. As a result, the coating exhibits better adhesion.

Although, as the coating, the porous coating including the deposit of fibers has been described above, the form of the coating is not limited thereto. A continuous coating having no pores may be formed, and a porous coating in a form other than the deposit of fibers, for example, a porous coating obtained by forming a plurality of through pores irregularly or regularly in a continuous coating, that is, a discontinuous coating, may be formed. As described above, a coating having a desired shape can be formed by adjusting the viscosity of the spray composition, the distance between the nozzle and the skin, the voltage applied to the nozzle, and the like.

Although the distance between the nozzle and the skin depends on the voltage applied to the nozzle, the distance of 50 mm or more and 150 mm or less is preferable in order to successfully form the coating. The distance between the nozzle and the skin can be measured using a commonly used non-contact sensor or the like.

Regardless of whether or not the coating formed with the electrostatic spraying method is a porous coating, the basis weight of the coating is preferably $0.1 \text{ g/m}^2$ or greater, and more preferably $1 \text{ g/m}^2$ or greater. In addition, the basis weight is preferably $30 \text{ g/m}^2$ or less, and more preferably $20 \text{ g/m}^2$ or less. For example, the basis weight of the coating is preferably from $0.1 \text{ g/m}^2$ to $30 \text{ g/m}^2$, and more preferably from $1 \text{ g/m}^2$ to $20 \text{ g/m}^2$. Setting the basis weight of the coating in this manner makes it possible to effectively prevent color transfer of the base-make up cosmetics in the cosmetics application region, while preventing the coating from coming off as a result of the coating becoming too thick.

The electrostatic spraying step of electrostatically spraying a composition directly onto skin, thereby forming a coating refers to a step of electrostatically spraying a composition on skin onto which the cosmetics have been applied (may simply be referred to as skin), thereby forming a coating. A step of electrostatically spraying a composition on a region other than skin, thereby forming a sheet composed of fibers, and then applying the sheet to the skin is different from the above-described electrostatic spraying step. Note that, prior to or subsequent to application of the cosmetics onto the skin, cosmetics other than the above-described cosmetics may be applied.

The present invention may include a liquid agent applying step of applying a liquid agent containing one or more selected from water, polyols, and oils that are in liquid form at 20° C. on the skin onto which the cosmetics have been applied, prior to or subsequent to or both prior to and subsequent to the electrostatic spraying step of forming the coating on the cosmetics application region using the above-described electrostatic spraying. When the liquid agent applying step is performed, the coating formed in the electrostatic spraying step easily bonds with the cosmetics application region. Therefore, the coating comes into highly intimate contact with the skin, and the transparency is improved. For example, a level difference is unlikely to be generated between the end portion of the coating and the skin, and thus the adhesion between the coating and the skin is improved. As a result, the coating is unlikely to come off or crack. Furthermore, the colors of the make-up cosmetics are barely concealed, and a more natural appearance is obtained, and the coating is difficult to visually confirm. When the coating is a porous coating composed of a deposit of fibers, which is a more preferable embodiment, adhesion to the skin is high despite being of high porosity, and a large capillary force is likely to be generated. Furthermore, use of fine fibers makes it easy to increase the specific surface area of the porous coating.

In particular, by performing the liquid agent applying step subsequent to the step of forming a porous coating composed of a deposit of fibers in the electrostatic spraying step, a moisturizing liquid agent holding coating in which the liquid agent is present between the fibers included in the porous coating and/or on the surfaces of the fibers is formed. Accordingly, the adhesion of the coating is improved, and the transparency of the coating when visually confirmed is maintained or improved. In particular, when the coating is colorless and transparent or colored and transparent, the coating is difficult to visually confirm, and thus can be made to look like natural skin. When the coating is colored and transparent, the coating has a feeling of transparency and thus can be made to look like part of the skin.

When the liquid agent to be used in the liquid agent applying step contains water, examples of the liquid agent include liquids such as water, an aqueous solution, and an aqueous dispersion, gels thickened using a thickener, polar oils, oil agents containing 10 mass % or greater of polar oil, and polar oil-containing emulsions (O/W emulsions and W/O emulsions).

When the liquid agent to be used in the liquid agent applying step includes polyols, examples of the polyols include alkylene glycols such as ethylene glycol, propylene glycol, 1, 3-propanediol, and 1, 3-butandiol; polyalkylene glycols such as diethylene glycol, dipropylene glycol, polyethylene glycol and polypropylene glycol; glycerins such as glycerin, diglycerin and triglycerin. Of these, from the viewpoint of usability such as smooth application, ethylene glycol, polyethylene glycol, 1, 3-butandiol, dipropylene glycol, polyethylene glycol, glycerin and diglycerin are preferable, and propylene glycol and 1, 3-butandiol are more preferable.

On the other hand, when the liquid agent to be used in the liquid agent applying step includes an oil that is in a liquid form at 20° C. (this oil is also referred to as "liquid oil" hereinafter), examples of the oil, which is in a liquid form at 20° C., include linear or branched hydrocarbon oils such as liquid paraffin, light isoparaffin, liquid isoparaffin, squalane, and squalene; ester oils such as a plant oil including jojoba oil and olive oil, an animal oil including liquid lanolin, monoalcohol fatty acid ester, and polyhydric alcohol fatty acid ester; and silicone oils such as dimethylpolysiloxane, dimethylcyclopolysiloxane, methylphenylpolysiloxane, methylhydrogenpolysiloxane, and higher alcohol modified organopolysiloxane. Of these, from the viewpoint of usability such as smooth application, the hydrocarbon oils and polar oils such as the ester oils, the plant oils containing a triglyceride etc., and the silicone oils are preferable, and the hydrocarbon oils, the ester oils, and the triglyceride are more preferable. The liquid oils selected from these oils can be used alone or in combination of two or more.

Examples of the above-mentioned hydrocarbon oils include liquid paraffin, squalane, squalene, n-octane, n-heptane, cyclohexane, light isoparaffin, and liquid isoparaffin, and liquid paraffin and squalane are preferable from the viewpoint of usability. The viscosities of the hydrocarbon oils at 30° C. are preferably 10 mPa·s or more, and more preferably 30 mPa·s or more, from the viewpoint of bringing the electrostatically sprayed coating into intimate contact with the skin. From these viewpoints, the total content of isododecane, isohexadecane, and hydrogenated polyisobutene, which have a viscosity of less than 10 mPa·s at 30° C., in the liquid agent is preferably 10 mass % or less, more preferably 5 mass % or less, even more preferably 1 mass % or less, and even more preferably 0.5 mass % or less, or alternatively, none of these oils need to be contained in the liquid agent.

Similarly, from the viewpoint of bringing the electrostatically sprayed coating into intimate contact with the skin, a viscosity of the ester oil and silicone oil is preferably 10 mPa·s at more, and more preferably 30 mPa·s or more at 30° C.

Here, the viscosity is measured using a BM type viscometer (manufactured by Tokimec Inc.; measurement condition: rotor No. 1, 60 rpm, 1 minute) at 30° C. It should be noted that from the same viewpoint, the total content of ether oils such as cetyl-1,3-dimethyl butyl ether, dicapryl ether, dilauryl ether, diisostearyl ether in the liquid agent is preferably 10 mass % or less, more preferably 5 mass % or less, and even more preferably 1 mass % or less.

Polar oils that are in a liquid form at 20° C. can be preferably used as the above-mentioned liquid oil, and examples thereof include ester oils, plant oils (triglycerides), higher alcohols of branched fatty acids or unsaturated fatty acids, antiseptics, and silicone oils. These liquid oils can be used alone or in combination of two or more.

Examples of the above-mentioned ester oils include esters between a linear or branched fatty acid and a linear or branched alcohol or a polyhydric alcohol. Specific examples thereof include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrite tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalene dicarboxylic acid, (12- to 15-carbon) alkyl benzoate, cetearylisononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, glyceryl tri-palm oil fatty acid, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyllaurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl p-methoxycinnamate, and tripropylene glycol dipivalate.

From the viewpoint of bringing the electrostatically sprayed coating into intimate contact with the skin and from the viewpoint of great feeling when applied on the skin, the ester oil preferably includes at least one ester oil selected from octyldodecyl myristate, myristyl myristate, isocetyl stearate, isocetyl isostearate, cetearylisononanoate, diisobutyl adipate, di-2-ethylhexyl sebacate, isopropyl myristate, isopropyl palmitate, diisostearyl malate, neopentyl glycol dicaprate, (12- to 15-carbon) alkyl benzoate, and glycerin tri(caprylate/caprate), more preferably includes at least one ester oil selected from isopropyl myristate, isopropyl palmitate, diisostearyl malate, neopentyl glycol dicaprate, (12- to 15-carbon) alkyl benzoate, and glycerin tri(caprylate/caprate), and even more preferably includes at least one ester oil selected from neopentyl glycol dicaprate, (12- to 15-carbon) alkyl benzoate, and glycerin tri(caprylate/caprate).

Fatty acid triglycerides are preferable as the triglyceride, and are contained in olive oil, jojoba oil, macadamia nut oil, meadowfoam oil, castor oil, safflower oil, sunflower oil, avocado oil, canola oil, apricot kernel oil, rice germ oil, and rice oil, for example.

Examples of the higher alcohols include liquid higher alcohols with 12 to 20 carbon atoms, and specific examples thereof include isostearyl alcohol and oleyl alcohol.

Examples of the antiseptics include phenoxyethanol, methyl p-hydroxybenzoate, ethyl p-aminobenzoate, isobutyl p-hydroxybenzoate, isopropyl p-hydroxybenzoate, ethyl p-hydroxybenzoate, butyl p-hydroxybenzoate, propyl p-hydroxybenzoate, benzyl p-hydroxybenzoate, and ethyl hexanediol.

Examples of the silicone oils include dimethylpolysiloxane, dimethylcyclopolysiloxane, methylphenylpolysiloxane, methylhydrogenpolysiloxane, and higher alcohol modified organopolysiloxane.

The kinetic viscosities of the silicone oils at 25° C. are preferably 3 mm$^2$/s, more preferably 4 mm$^2$/s, and even more preferably 5 mm$^2$/s or greater, and are preferably 30 mm$^2$/s or less, more preferably 20 mm$^2$/s or less, and even more preferably 10 mm$^2$/s or less, from the viewpoint of bringing the electrostatically sprayed coating into intimate contact with the skin.

Of these, from the viewpoint of bringing the electrostatically sprayed coating into intimate contact with the skin, dimethylpolysiloxane is preferably contained.

It is preferable that the liquid agent contains a liquid oil, and the content of the liquid oil in the liquid agent is preferably 0.1 mass % or greater, more preferably 0.5 mass % or greater, and even more preferably 5 mass % or greater. In addition, the content thereof is preferably 100 mass % or less. The content of the liquid oil in the liquid agent is preferably from 0.1 to 100 mass %, and more preferably from 0.5 to 100 mass %.

When the liquid agent contains the polar oil, it is preferable that the liquid agent contains water and the polar oil from the viewpoint of enhancing the adhesion of the coating to the skin, and the total content of water and the polar oil in the liquid agent is preferably 40 mass % or more and 100 mass % or less. Also, from the viewpoint of stability, the liquid agent may contain a surfactant, a polymer, and a thickener, and from the viewpoint of improving the adhesion to the skin and the moisturizing performance with respect to the coating, the liquid agent may contain an oil agent that is in a solid form at 30° C., such as vaseline, cetanol, stearyl alcohol, and ceramide.

From similar view points, when the liquid agent contains the polyol, it is preferable that the liquid agent contains water and the polyol from the viewpoint of enhancing the adhesion of the coating to the skin, and the total content of water and the polyol in the liquid agent is preferably 40 mass % or more and 100 mass % or less. Also, from the viewpoint of stability, the liquid agent may contain a surfactant, a polymer, and a thickener, and from the viewpoint of improving the adhesion to the skin and the moisturizing performance with respect to the coating, the liquid agent may contain an oil agent that is in a solid form at 30° C., such as vaseline, cetanol, stearyl alcohol, and ceramide.

Even when one of water, polyol and the liquid oil is used in the liquid agent, it is preferable that the liquid agent has a viscosity of about 5,000 mPa·s or less at 25° C. from the viewpoint of improving the adhesion of the coating formed with the electrostatic spraying method to the skin. The viscosity of the liquid is measured with the method as described above.

Furthermore, from the viewpoint of improving the adhesion of the coating formed with the electrostatic spraying method to the skin, the content of the coloring pigments in the liquid is preferably 0.1 mass % or less, more preferably 0.05 mass % or less, and even more preferably 0.001 mass % or less. In the present invention, the coloring pigment doesn't include transparent pigment, and white pigment is included in the coloring pigment.

The liquid agent including water, polyol or the liquid oil can be applied on the skin with various methods. For example, a thin layer of the liquid agent can be formed by applying the liquid agent on the skin with a dripping method, a sprinkling method, or the like, and performing a step of spreading the liquid agent to cause the liquid agent to bond with the skin or the coating. In the step of spreading the liquid agent, a method such as smearing using the user's own finger, a tool such as an applicator, or the like can be applied, for example. Although it is sufficient if the liquid agent is merely dripped or sprinkled, performing the spreading step makes it possible to cause the liquid agent to bond with the skin or the coating, thus making it possible to sufficiently improve the adhesion of the coating. As another method, a thin layer of the liquid agent can be formed by spraying the liquid agent on the skin. In this case, it is not particularly necessary to separately spread the liquid agent, but a spreading operation may be performed after spraying. It should be noted that when the liquid agent is applied after the coating is formed, a sufficient amount of the liquid agent is applied on the skin, and excessive liquid agent can be removed by performing a step of bringing a sheet material into contact with an area on which the liquid agent has been applied.

It is sufficient if the amount of the liquid agent applied on the skin or the coating is set to be a necessary and sufficient amount with which the adhesion between the skin and the coating is improved. When the liquid agent contains the liquid oil, from the viewpoint of obtaining reliable adhesion between the skin and the coating, the amount of the liquid agent applied on the skin is set such that the basis weight of the liquid oil is preferably 0.1 $g/m^2$ or more, and more preferably 0.2 $g/m^2$ or more, and in addition, the basis weight of the liquid oil is preferably 40 $g/m^2$ or less, and more preferably 35 $g/m^2$ or less. The amount of the liquid agent applied on the skin is set such that the basis weight of the liquid oil is preferably 0.1 $g/m^2$ or more and 40 $g/m^2$ or less, and more preferably 0.2 $g/m^2$ or more and 35 $g/m^2$ or less.

From the viewpoint of improving the adhesion between the skin and the coating and improving the transparency, the amount of the liquid agent applied on the skin or the coating is preferably 5 $g/m^2$ or more, more preferably 10 $g/m^2$ or more, and even more preferably 15 $g/m^2$ or more, and in addition, the amount is preferably 50 $g/m^2$ or less, and more preferably 45 $g/m^2$ or less. Furthermore, the cosmetics other than the liquid agent may be applied on the skin before or after the liquid agent is applied.

The coating formation method as described above is useful as various beauty treatment methods that are not intended to be used as a method of performing operation, treatment, or diagnosis of a human body. For the purpose of beauty treatment, the coating formation method according to the present invention can be applied to whitening of skin at the cosmetics application region, concealment of specks on skin, concealment of dullness/dark areas of skin, concealment of wrinkles of skin, shading of skin, protection of skin from ultraviolet rays, and moisturization of skin, for example.

Although the present invention has been described based on the preferred embodiment above, the present invention is not limited to the above-mentioned embodiment. In the above-mentioned embodiment, a person who wants to form a coating on his/her skin holds the electrostatic spraying apparatus 10 and generates an electric field between the conductive nozzle of the apparatus 10 and his/her skin, for example. However, a person who wants to form a coating on his/her skin need not hold the electrostatic spraying apparatus 10 as long as an electric field is generated between the conductive nozzle and the skin.

With respect to the above-described embodiment, the present invention further discloses the following aspects of the coating formation method.

<1>

A coating formation method including an electrostatic spraying step of electrostatically spraying a composition directly onto a skin surface onto which powder-containing cosmetics have been coated, thereby forming a coating on the skin, wherein the composition contains a component (a) and a component (b) below:

(a) one or more volatile substances selected from water, alcohols, and ketones; and (b) a polymer having a coating formation ability.

<2>

The coating formation method as set forth in clause <1>, further including a liquid agent applying step of applying a liquid agent containing one or more selected from water, polyols, and oils that are in liquid form at 20° C. on the skin onto which the cosmetics have been coated, wherein the liquid agent applying step is performed subsequent to the electrostatic spraying step.

<3>

The coating formation method as set forth in clause <2>, wherein, in a case where the liquid agent to be used in the liquid agent applying step contains water, the liquid agent is one or more selected from liquids such as water, an aqueous solution, and an aqueous dispersion, gels thickened using a thickener, polar oils, oil agents containing 10 mass % or greater of polar oil, and polar oil-containing emulsions (O/W emulsions and W/O emulsions).

<4>

The coating formation method as set forth in clause <2> or <3>, wherein, in a case where the liquid agent to be used in the liquid agent applying step contains an oil that is in liquid form at 20° C., examples of the oil include: linear or branched hydrocarbon oils such as liquid paraffin, light isoparaffin, liquid isoparaffin, squalane, and squalene; ester oils such as a plant oil including jojoba oil and olive oil, an animal oil including liquid lanolin, monoalcohol fatty acid ester, and polyhydric alcohol fatty acid ester; and silicone oils such as dimethylpolysiloxane, dim ethyl cyclopolysiloxane, methylphenylpolysiloxane, methylhydrogenpolysiloxane, and higher alcohol modified organopolysiloxane, and, of these, the oil is one or more selected preferably from hydrocarbon oils and polar oils such as ester oils, plant oils containing a triglyceride etc., and silicone oils, and more preferably from hydrocarbon oils, ester oils, and triglyceride.

<5>

The coating formation method as set forth in clause <4>, wherein the hydrocarbon oils are one or more selected from liquid paraffin, squalane, squalene, n-octane, n-heptane, cyclohexane, light isoparaffin, and liquid isoparaffin, and preferably one or more selected from liquid paraffin and squalane.

<6>

The coating formation method as set forth in clause <4>, wherein examples of the ester oils include esters between a linear or branched fatty acid and a linear or branched alcohol or a polyhydric alcohol, and specific examples thereof include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrite tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalene dicarboxylic acid, (12- to 15-carbon) alkyl benzoate, cetearylisononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, glyceryl tri-palmoil fatty acid, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyllaurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl p-methoxycinnamate, and tripropylene glycol dipivalate.

<7>

The coating formation method as set forth in clause <4>, wherein the triglyceride is preferably a fatty acid triglyceride, and examples thereof include olive oil, jojoba oil, macadamia nut oil, meadowfoam oil, castor oil, safflower oil, sunflower oil, avocado oil, canola oil, apricot kernel oil, rice germ oil, and rice bran oil.

<8>

The coating formation method as set forth in clause <4>, wherein examples of the higher alcohol include liquid higher alcohols with 12 to 20 carbon atoms, and specific examples thereof include isostearyl alcohol and oleyl alcohol.

<9>

The coating formation method as set forth in clause <4>, wherein examples of the antiseptics include phenoxyethanol, methyl p-hydroxybenzoate, ethyl p-aminobenzoate, isobutyl p-hydroxybenzoate, isopropyl p-hydroxybenzoate, ethyl p-hydroxybenzoate, butyl p-hydroxybenzoate, propyl p-hydroxybenzoate, benzyl p-hydroxybenzoate, and ethyl hexanediol.

<10>

The coating formation method as set forth in clause <4>, wherein examples of the silicone oils include dimethylpolysiloxane, dimethylcyclopolysiloxane, methylphenylpolysiloxane, methylhydrogenpolysiloxane, and higher alcohol modified organopolysiloxane.

<11>

The coating formation method as set forth in any one of clauses <2> to <10>, wherein the liquid agent preferably contains a liquid oil, and the content of the liquid oil in the liquid agent is preferably 0.1 mass % or greater, more preferably 0.5 mass % or greater, and even more preferably 5 mass % or greater, is preferably 100 mass % or less, and is preferably from 0.1 to 100 mass %, and more preferably from 0.5 to 100 mass %.

<12>

The coating formation method as set forth in any one of clauses <2> to <11>, wherein, in a case where the liquid agent contains a polar oil, the liquid agent contains water and a polar oil, and preferably contains water and a polar oil in a total amount of from 40 to 100 mass %.

<13>

The coating formation method as set forth in any one of clauses <2> to <12>, wherein the liquid agent may contain a surfactant, a polymer, and a thickener, and may contain an oil agent that is in solid form at 30° C., such as Vaseline, cetanol, stearyl alcohol, and ceramide.

<14>

The coating formation method as set forth in any one of clauses <2> to <13>, wherein, in the electrostatic spraying step, a porous coating composed of a deposit of fibers is formed, and in the subsequent liquid agent applying step, a moisturizing liquid agent holding coating in which a moisturizing liquid agent is present between the fibers included in the coating and/or on surfaces of the fibers is formed by applying the liquid agent onto the coating formed on the skin onto which the powder-containing cosmetics have been coated.

<15>

The coating formation method as set forth in any one of clauses <2> to <14>, wherein, in the liquid agent applying step, the transparency of the coating is maintained by applying the liquid agent onto the coating formed on the skin onto which the powder-containing cosmetics have been coated.

<16>

The coating formation method as set forth in any one of clauses <1> to <15>, wherein, in the electrostatic spraying step, the composition is electrostatically sprayed onto the skin to form a porous coating.

<17>

The coating formation method as set forth in any one of clauses <1> to <16>, wherein in the electrostatic spraying step, an electrostatic spraying apparatus is used to electrostatically spray the composition on the skin to form a porous coating including a deposit of fibers, and the electrostatic spraying apparatus comprises:
a container in which the composition is accommodated;
a nozzle from which the composition is discharged;
a supply device that supplies the composition accommodated in the container to the nozzle; and
a power source that applies a voltage to the nozzle.

<18>
The coating formation method as set forth in any one of clauses <1> to <17>, wherein the vapor pressure of the volatile substance of (a) at 20° C. is preferably 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.

<19>
The coating formation method as set forth in any one of clauses <1> to <18>, wherein the volatile substance of (a) is alcohol, chain aliphatic monohydric alcohols, cyclic aliphatic monohydric alcohols, and aromatic monohydric alcohols are preferably used as the alcohol, these alcohols can be used alone or in combination of two or more, and ethanol, isopropyl alcohol, butyl alcohol, phenylethyl alcohol, propanol, and pentanol are particularly preferably used as the alcohol.

<20>
The coating formation method as set forth in any one of clauses <1> to <19>, wherein the volatile substance of (a) is at least one member selected from ethanol, isopropyl alcohol, butyl alcohol, and water, preferably at least one member selected from ethanol and butyl alcohol, and more preferably ethanol.

<21>
The coating formation method as set forth in any one of clauses <1> to <20>, wherein the polymer of (b) having a coating formation ability is a substance that can be dissolved in the volatile substance of (a) and includes water-soluble polymers and water-insoluble polymers, and here, the term "dissolve" refers to a state in which a substance is in a dispersed state at 20° C. and the dispersion is uniform when visually observed, and preferably transparent or translucent when visually observed.

<22>
The coating formation method as set forth in clause <21>, wherein the water-soluble polymers having a coating formation ability are one or more water-soluble macromolecules selected from naturally-occurring polymers such as pullulan, hyaluronic acid, chondroitin sulfate, poly-γ-glutamic acid, modified corn starch, β-glucan, glucooligosaccharide, mucopolysaccharide such as heparin and keratosulfate, cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, hydroxypropyl methyl cellulose; partially saponified polyvinyl alcohol (when not used in combination with a cross-linking agent); low saponified polyvinyl alcohol; polyvinyl pyrrolidone (PVP); polyethylene oxide; and sodium polyacrylate, and preferably one or more water-soluble macromolecules selected from pullulan, partially saponified polyvinyl alcohol, low saponified polyvinyl alcohol, polyvinyl pyrrolidone, and polyethylene oxide.

<23>
The coating formation method as set forth in clause <21>, wherein the water-insoluble polymers having a coating formation ability are one or more water-insoluble polymers selected from completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethyl siloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin, and preferably one or more water-insoluble polymers selected from completely saponified polyvinyl alcohol, which can be insolubilized after the formation of a coating, partially saponified polyvinyl alcohol, which can be cross-linked after the formation of the nanofiber when used in combination with a cross-linking agent, a polyvinyl butyral resin, oxazoline modified silicone such as a γ poly(N-propanoylethyleneimine)-grafted dimethylsiloxane/γ-aminopropylmethylsiloxane copolymer, water-soluble polyester, and zein.

<24>
The coating formation method as set forth in any one of clauses <1> to <23>, wherein the content of the component (a) in the composition is preferably 50 mass % or more, more preferably 55 mass % or more, and even more preferably 60 mass % or more, the content of the component (a) in the composition is preferably 98 mass % or less, 96 mass % or less, and 94 mass % or less, and the content of the component (a) in the composition is preferably 50 mass % or more and 98 mass % or less, more preferably 55 mass % or more and 96 mass % or less, and even more preferably 60 mass % or more and 94 mass % or less.

<25>
The coating formation method as set forth in any one of clauses <1> to <24>, wherein the content of the component (b) in the composition is preferably 2 mass % or more, more preferably 4 mass % or more, and even more preferably 6 mass % or more, the content of the component (b) in the composition is preferably 50 mass % or less, more preferably 45 mass % or less, and even more preferably 40 mass % or less, and the content of the component (b) in the composition is preferably 2 mass % or more and 50 mass % or less, more preferably 4 mass % or more and 45 mass % or less, and even more preferably 6 mass % or more and 40 mass % or less.

<26>
The coating formation method as set forth in any one of clauses <1> to <25>, wherein the composition includes only the component (a) and component (b) or includes other components in addition to the component (a) and the component (b), and the other components include a plasticizer for the polymer of (b) having a coating formation ability, a coloring pigment, an extender pigment, a dye, a surfactant, a UV protection agent, a flavoring agent, a repellent, an antioxidant, a stabilizer, an antiseptic, and various vitamins.

<27>
The coating formation method as set forth in clause <26>, wherein when the composition includes the other components, the blend proportion of the other components is preferably 0.1 mass % or more and 30 mass % or less, and more preferably 0.5 mass % or more and 20 mass % or less.

<28>

The coating formation method as set forth in any one of clauses <1> to <27>, wherein the viscosity of the composition is preferably 1 mPa·s or more, more preferably 10 mPa·s or more, and even more preferably 50 mPa·s or more, at 25° C., the viscosity of the composition is preferably 5,000 mPa·s or less, more preferably 2,000 mPa·s or less, and even more preferably 1,500 mPa·s or less, at 25° C., and the viscosity of the composition is preferably 1 mPa·s or more and 5,000 mPa·s or less, more preferably 10 mPa·s or more and 2,000 mPa·s or less, and even more preferably 50 mPa·s or more and 1,500 mPa·s or less, at 25° C.

<29>

The coating formation method as set forth in any one of clauses <1> to <28>, wherein an electrostatic spraying method is performed using an electrostatic spraying apparatus, the electrostatic spraying apparatus includes the nozzle, and the nozzle is made of a conductor including various conductors typified by metal or a non-conductor such as plastic, rubber, or ceramic and has a shape allowing the composition to be discharged from the tip of the nozzle.

<30>

The coating formation method as set forth in any one of clauses <1> to <29>, wherein the electrostatic spraying method is performed using an electrostatic spraying apparatus, the electrostatic spraying apparatus includes the nozzle and a housing, the nozzle is arranged at one end, in a longitudinal direction, of the housing, and the nozzle is arranged in the housing in such a manner that the direction in which the composition is discharged matches the longitudinal direction of the housing and the nozzle projects toward the skin.

<31>

The coating formation method as set forth in any one of clauses <1> to <30>, wherein in the sprayed composition, the volatile substance used as a solvent is evaporated from droplets, and the polymer having a coating formation ability used as a solute is solidified to form fibers while the fibers are stretched and deformed due to an electric potential difference.

<32>

The coating formation method as set forth in any one of clauses <1> to <31>, wherein the electrostatic spraying method is performed using an electrostatic spraying apparatus, the electrostatic spraying apparatus includes the nozzle, and the distance between the nozzle and the skin is set to be 50 mm or more and 150 mm or less.

<33>

The coating formation method as set forth in any one of clauses <1> to <32>, wherein the basis weight of the coating formed with the electrostatic spraying method is preferably 0.1 g/m² or more, and more preferably 1 g/m² or more, the basis weight of the coating is preferably 30 g/m² or less, and more preferably 20 g/m² or less, and the basis weight of the coating is preferably 0.1 g/m² or more and 30 g/m² or less, and more preferably 1 g/m² or more and 20 g/m² or less.

<34>

The coating formation method as set forth in any one of clauses <2> to <33>, wherein, in a case where the liquid agent to be used in the liquid agent applying step contains water, the liquid agent is one or more selected from liquids such as water, an aqueous solution, and an aqueous dispersion, gels thickened using a thickener, polar oils, oil agents containing 10 mass % or greater of polar oil, and polar oil-containing emulsions (O/W emulsions and W/O emulsions).

<35>

The coating formation method as set forth in any one of clauses <2> to <34>, wherein when the liquid agent to be used in the liquid agent applying step includes an oil that is in a liquid form at 20° C., examples of the oil include linear or branched hydrocarbon oils such as liquid paraffin, light isoparaffin, liquid isoparaffin, squalane, and squalene, ester oils such as a plant oil including jojoba oil and olive oil, an animal oil including liquid lanolin, monoalcohol fatty acid ester, and polyhydric alcohol fatty acid ester; and silicone oils such as dimethylpolysiloxane, dimethylcyclopolysiloxane, methylphenylpolysiloxane, methylhydrogenpolysiloxane, and higher alcohol modified organopolysiloxane, and the oil is one or more selected preferably from the hydrocarbon oils and polar oils such as the ester oils, the plant oils containing a triglyceride etc., and the silicone oils, and more preferably from the hydrocarbon oils, the ester oils, and the triglyceride.

<36>

The coating formation method as set forth in any one of clauses <2> to <35>, wherein it is preferable that the liquid agent contains the liquid oil, the content of the liquid oil in the liquid agent is preferably 0.1 mass % or more, more preferably 0.5 mass % or more, and even more preferably 5 mass % or more, the content of the liquid oil in the liquid agent is preferably 100 mass % or less, and the content of the liquid oil in the liquid agent is preferably 0.1 mass % or more and 100 mass % or less, more preferably 0.5 mass % or more and 100 mass % or less, and even more preferably 5 mass % or more and 100 mass % or less.

<37>

The coating formation method as set forth in any one of clauses <2> to <36>, wherein when the liquid agent contains the polar oil, it is preferable that the liquid agent contains water and the polar oil, and that the total content of water and the polar oil is preferably 40 mass % or more and 100 mass % or less.

<38>

The coating formation method as set forth in any one of clauses <2> to <37>, wherein it is preferable that the liquid agent contains a surfactant, a polymer, and a thickener, and that the liquid agent contains an oil agent that is in a solid form at 30° C., such as vaseline, cetanol, stearyl alcohol, and ceramide.

<39>

The coating formation method as set forth in any one of clauses <2> to <38>, wherein when the liquid agent contains the liquid oil, the amount of the liquid agent applied on the skin is set such that the basis weight of the liquid oil is preferably 0.1 g/m² or more, and more preferably 0.2 g/m² or more, the basis weight is preferably 40 g/m² or less, and more preferably 35 g/m² or less, and the basis weight is preferably 0.1 g/m² or more and 40 g/m² or less, and more preferably 0.2 g/m² or more and 35 g/m² or less, and the amount of the liquid agent applied on the skin or the coating is preferably 5 g/m² or more, more preferably 10 g/m² or more, and even more preferably 15 g/m² or more, and the amount is preferably 50 g/m² or less, and more preferably 45 g/m² or less.

EXAMPLES

Hereinafter, the present invention will be described more specifically by way of examples. However, the scope of the present invention is not limited to these examples. Unless otherwise stated, "%" means "mass %".

Test Example 1

Example 1

(1) Application of Base-Make Up Cosmetics

A powder foundation shown in Table 1 below was used. This foundation was applied onto the back of a person's hand.

(2) Preparation of Spray Composition 99.5% Ethanol was used as the component (a) of the spray composition. Polyvinyl butyral was used as the component (b). Di(phytosteryl/octyl dodecyl)lauroyl glutamate (manufactured by Ajinomoto Co., Inc., Eldew PS-203) was used as another component. The blend proportion of ethanol as the component (a) was 80%, that of the component (b) was 14%, and that of di(phytosteryl/octyl dodecyl)lauroyl glutamate as the other component was 6%.

(3) Electrostatic Spraying Step

The electrostatic spraying method was performed for 20 seconds onto a cosmetics application region, using the electrostatic spraying apparatus 10 having the configuration shown in FIG. 1 and the external appearance shown in FIG. 2. The electrostatic spraying method was performed under the conditions described below.

Applied voltage: 10 kV
Distance between conductive nozzle and skin: 100 mm
Discharge amount of spray composition: 5 ml/h
Environment: 25° C., 30% RH A porous coating composed of a deposit of fibers was formed spanning the entire cosmetics application region with this electrostatic spraying. The coating had a circular shape with a diameter of about 4 cm, and had a mass of about 5.5 mg. The thickness of the fibers measured using the above-described method was 506 nm.

Example 2

A cream foundation shown in Table 1 was used as base-make up cosmetics. A porous coating composed of a deposit of fibers was obtained as in Example 1, except for this aspect.

Example 3

A liquid foundation shown in Table 1 was used as base-make up cosmetics. The electrostatic spraying was performed immediately after the application of the liquid foundation. The component (b) in the spray composition was as shown in Table 2. A porous coating composed of a deposit of fibers was obtained as in Example 1, except for this aspect.

Example 4

A concealer shown in Table 1 was used as base-make up cosmetics. The component (b) in the spray composition was as shown in Table 2. A porous coating composed of a deposit of fibers was obtained as in Example 1, except for this aspect.

Example 5

After a porous coating composed of a deposit of fibers was formed on the surface of the cosmetics application region in the electrostatic spraying step in Example 1, a liquid agent applying step of applying a liquid agent was performed. In the liquid agent applying step, 80 mg of a cosmetic milky lotion A was used as the liquid agent. Table 4 shows the composition of the cosmetic milky lotion A. The cosmetic milky lotion A was spread so as to have an area with a diameter of 4 cm or greater and less than 6 cm (diameter 5 cm) using a finger, and allowed to bond with the cosmetics application region, so that a thin layer was thus formed on the coating. The amount of the dripped cosmetic milky lotion A was 80 mg, and the amount was such that the presence of the cosmetic milky lotion A could be confirmed by visual observation or by touch due to the region in which the cosmetic milky lotion A was spread being wet or moist, or having a different texture, or the like. As a result, the amount of the cosmetic milky lotion A applied onto the skin was set such that the basis weight of the cosmetic milky lotion A was 40.8 g/m$^2$ and the total basis weight of the liquid oil contained in the cosmetic milky lotion A was 15.3 g/m$^2$.

Examples 6 to 16

After a porous coating composed of a deposit of fibers was formed on the surface of the cosmetics application region in the electrostatic spraying step in Examples 2 to 4, a liquid agent applying step of applying a liquid agent was performed. In the liquid agent applying step, the cosmetic milky lotion A as in Example 5 was used as the liquid agent. The procedure was as in Example 5, except for this aspect.

Example 17

In Example 17, 100% ethanol and water were used instead of 99.5% ethanol aqueous solution in Example 5. A porous coating composed of a deposit of fibers was obtained as in Example 5, except for this aspect.

Comparative Examples 1 to 4

In the comparative examples, the electrostatic spraying step was not performed in Examples 1 to 4, and thus the cosmetics application region was left exposed.

Comparative Example 5

(1) Application of Base-Make Up Cosmetics

A powder foundation shown in Table 1 below was used. This foundation was applied onto the back of a person's hand.

(2) Preparation of Spray Composition 99.5% Ethanol and 1-butanol were used as the component (a) of the spray composition. Polyvinyl butyral was used as the component (b). The blend proportions of ethanol and 1-butanol as the component (a) were respectively 62% and 24%, and that of polyvinyl butyral as the component (b) was 14%.

(3) Formation of Sheet in the Electrostatic Spraying Step

The electrostatic spraying method was performed for 20 seconds onto a stainless steel plate, using the electrostatic spraying apparatus 10 having the configuration shown in FIG. 1 and the external appearance shown in FIG. 2. The electrostatic spraying method was performed under the conditions described below.

Applied voltage: 10 kV
Distance between nozzle and skin: 100 mm
Discharge amount of spray composition: 5 ml/h
Environment: 25° C., 30% RH A porous coating composed of a deposit of fibers was formed on the surface of the stainless steel plate with this electrostatic spraying. The coating had a circular shape with a diameter of about 4 cm, and had a mass of about 5.5 mg. The thickness of the fibers measured using the above-described method was 506 nm.

(4) Sheet Applying Step

The sheet obtained in the electrostatic spraying step (3) was detached from the stainless steel plate, softly placed on the skin onto which the foundation has been applied in the step (1), and gently pressed.

(5) Liquid Agent Applying Step

A liquid agent applying step of applying a liquid agent was performed immediately after the sheet applying step (4). In the liquid agent applying step, 80 mg of a cosmetic milky lotion A was used as the liquid agent. Table 3 shows the composition of the cosmetic milky lotion A. The cosmetic milky lotion A was spread so as to have an area with a diameter of 4 cm or greater and less than 6 cm (diameter 5 cm) using a finger, and allowed to bond with the cosmetics application region, so that a thin layer was thus formed on the coating. The amount of the dripped cosmetic milky lotion A was 80 mg, and the amount was such that the presence of the cosmetic milky lotion A could be confirmed by visual observation or by touch due to the region in which the cosmetic milky lotion A was spread being wet or moist, or having a different texture, or the like. As a result, the amount of the cosmetic milky lotion A applied onto the skin was set such that the basis weight of the cosmetic milky lotion A was 40.8 g/m$^2$ and the total basis weight of the liquid oil contained in the cosmetic milky lotion A was 15.3 g/m$^2$.

Comparative Examples 6 to 8

In Comparative Examples 6 to 8, the spray compositions shown in Table 2 were used instead of those of Comparative Example 5. A porous coating composed of a deposit of fibers was obtained as in Comparative Example 5, except for this aspect.

Comparative Examples 9 to 12

In Comparative Examples 9 to 12, the order of the liquid agent applying step and the sheet applying step was reversed in Comparative Examples 5 to 8. A porous coating composed of a deposit of fibers was obtained as in Comparative Example 5, except for this aspect.

Evaluation

The effects of preventing cosmetic color transfer (sticking of colored cosmetics) to clothes at the coating formation region in the examples and comparative examples were evaluated. The evaluation was performed by wiping the center of the cosmetics application region five time with "K-Dry", which is paper wiper manufactured by Nippon Paper Crecia Co., Ltd., visually observing the degree of color transfer of the base-make up cosmetics to the paper wiper, and performing evaluation following the evaluation criteria below. In Examples 5 to 8, the evaluation was performed five minutes after the aftertreatment step of applying the liquid agent was complete. Tables 2 and 3 show the results.

4: The color of cosmetics was not seen on the paper wiper.
3: The color of cosmetics was slightly seen on the paper wiper.
2: The paper wiper was colored although the coloring degree was uneven.
1: The color of cosmetics was sufficiently seen on the paper wiper.

TABLE 1

| Base make up cosmetics | | Pigment content (mass %) |
|---|---|---|
| A | Sofina Primavista powder foundation UV | 12 |
| B | Sofina Primavista cream foundation | 25 |
| C | Sofina Primavista liquid foundation | 12 |
| D | Sofina Primavista concealer | 10 |

TABLE 2

| | | Base-make up cosmetics | Composition | | | Portion subjected to electrostatic spraying | Liquid agent | | Evaluation of color transfer prevention |
|---|---|---|---|---|---|---|---|---|---|
| | | | Component (a) (%) | Component (b) (%) | Others (%) | | Type | Application time | |
| Ex. | 1 | A | Ethanol (80) | Polyvinyl butyral (14) | Di(phytosteryl/octyl dodecyl)lauroyl glutamate (6) | Skin | None | | 4 |
| | 2 | B | Ethanol (80) | Polyvinyl butyral (14) | Di(phytosteryl/octyl dodecyl)lauroyl glutamate (6) | Skin | None | | 4 |
| | 3 | C | Ethanol (80) | Polyvinylacetal diethylamino acetate (14) | Di(phytosteryl/octyl dodecyl)lauroyl glutamate (6) | Skin | None | | 4 |
| | 4 | D | Ethanol (80) | Polyvinylacetal diethylamino acetate (14) | Di(phytosteryl/octyl dodecyl)lauroyl glutamate (6) | Skin | None | | 4 |
| | 5 | A | Ethanol (80) | Polyvinyl butyral (14) | Di(phytosteryl/octyl dodecyl)lauroyl glutamate (6) | Skin | Cosmetic milky lotion A | After electrostatic spraying | 4 |

TABLE 2-continued

| | Base-make up cosmetics | Composition | | | Portion subjected to electrostatic spraying | Liquid agent | | Evaluation of color transfer prevention |
|---|---|---|---|---|---|---|---|---|
| | | Component (a) (%) | Component (b) (%) | Others (%) | | Type | Application time | |
| 6 | B | Ethanol (80) | Polyvinyl butyral (14) | Di(phytosteryl/octyl dodecyl)lauroyl glutamate (6) | Skin | Cosmetic milky lotion A | After electrostatic spraying | 4 |
| 7 | C | Ethanol (80) | Polyvinylacetal diethylamino acetate (14) | Di(phytosteryl/octyl dodecyl)lauroyl glutamate (6) | Skin | Cosmetic milky lotion A | After electrostatic spraying | 4 |
| 8 | D | Ethanol (80) | Polyvinylacetal diethylamino acetate (14) | Di(phytosteryl/octyl dodecyl)lauroyl glutamate (6) | Skin | Cosmetic milky lotion A | After electrostatic spraying | 4 |
| 9 | A | Ethanol (88) | Polyvinyl butyral (10.5) | Di(phytosteryl/octyl dodecyl)lauroyl glutamate (1.5) | Skin | Cosmetic milky lotion A | After electrostatic spraying | 4 |
| 10 | B | Ethanol (88) | Polyvinyl butyral (10.5) | Di(phytosteryl/octyl dodecyl)lauroyl glutamate (1.5) | Skin | Cosmetic milky lotion A | After electrostatic spraying | 4 |
| 11 | C | Ethanol (88) | Polyvinyl butyral (10.5) | Di(phytosteryl/octyl dodecyl)lauroyl glutamate (1.5) | Skin | Cosmetic milky lotion A | After electrostatic spraying | 4 |
| 12 | D | Ethanol (88) | Polyvinyl butyral (10.5) | Di(phytosteryl/octyl dodecyl)lauroyl glutamate (1.5) | Skin | Cosmetic milky lotion A | After electrostatic spraying | 4 |
| 13 | A | Ethanol (62) 1-Butanol (24) | Polyvinyl butyral (14) | | Skin | Cosmetic milky lotion A | After electrostatic spraying | 4 |
| 14 | B | Ethanol (62) 1-Butanol (24) | Polyvinyl butyral (14) | | Skin | Cosmetic milky lotion A | After electrostatic spraying | 4 |
| 15 | C | Ethanol (62) 1-Butanol (24) | Polyvinyl butyral (14) | | Skin | Cosmetic milky lotion A | After electrostatic spraying | 4 |
| 16 | D | Ethanol (62) 1-Butanol (24) | Polyvinyl butyral (14) | | Skin | Cosmetic milky lotion A | After electrostatic spraying | 4 |
| 17 | A | 100% Ethanol (79.6) Water (0.4) | Polyvinyl butyral (14) | Di(phytosteryl/octyl dodecyl)lauroyl glutamate (6) | Skin | Cosmetic milky lotion A | After electrostatic spraying | 4 |

Ethanol: Ethanol (99.5), special grade (Wako Pure Chemical Industries, Ltd.)
1-Butanol: 1-Butanol, special grade (Wako Pure Chemical Industries, Ltd.)
Di(phytosteryl/octyl dodecyl)lauroyl glutamate: Eldew PS-203 (Ajinomoto Co., Inc.)
Polyvinyl butyral: S-LEC B BM-1 (Sekisui Chemical Co., Ltd.)
Polyvinylacetal diethylamino acetate: AEA (Mitsubishi-Kagaku Foods Corporation)

TABLE 3

| | | Base-make up cosmetics | Composition | | | Portion subjected to electrostatic spraying | Liquid agent | | Evaluation of color transfer prevention |
|---|---|---|---|---|---|---|---|---|---|
| | | | Component (a) (%) | Component (b) (%) | Others (%) | | Type | Application time | |
| Com. Ex. | 1 | A | None | | | — | None | | 2 |
| | 2 | B | None | | | — | None | | 1 |
| | 3 | C | None | | | — | None | | 1 |
| | 4 | D | None | | | — | None | | 2 |
| | 5 | A | Ethanol (62) 1-Butanol (24) | Polyvinyl butyral (14) | | Plate | Cosmetic milky lotion A | Before sheet application | 2 |
| | 6 | B | Ethanol (62) 1-Butanol (24) | Polyvinyl butyral (14) | | Plate | Cosmetic milky lotion A | Before sheet application | 1 |
| | 7 | C | Ethanol (62) 1-Butanol (24) | Polyvinyl butyral (14) | | Plate | Cosmetic milky lotion A | Before sheet application | 1 |
| | 8 | D | Ethanol (62) 1-Butanol (24) | Polyvinyl butyral (14) | | Plate | Cosmetic milky lotion A | Before sheet application | 2 |

TABLE 3-continued

| | Base-make up cosmetics | Composition | | | Portion subjected to electrostatic spraying | Liquid agent | | Evaluation of color transfer prevention |
|---|---|---|---|---|---|---|---|---|
| | | Component (a) (%) | Component (b) (%) | Others (%) | | Type | Application time | |
| 9 | A | Ethanol (62) 1-Butanol (24) | Polyvinyl butyral (14) | | Plate | Cosmetic milky lotion A | After sheet application | 2 |
| 10 | B | Ethanol (62) 1-Butanol (24) | Polyvinyl butyral (14) | | Plate | Cosmetic milky lotion A | After sheet application | 2 |
| 11 | C | Ethanol (62) 1-Butanol (24) | Polyvinyl butyral (14) | | Plate | Cosmetic milky lotion A | After sheet application | 2 |
| 12 | D | Ethanol (62) 1-Butanol (24) | Polyvinyl butyral (14) | | Plate | Cosmetic milky lotion A | After sheet application | 2 |

Ethanol: Ethanol (99.5), special grade (Wako Pure Chemical Industries, Ltd.)
1-Butanol: 1-Butanol, special grade (Wako Pure Chemical Industries, Ltd.)
Di(phytosteryl/octyl dodecyl)lauroyl glutamate: Eldew PS-203 (Ajinomoto Co., Inc.)
Polyvinyl butyral: S-LEC B BM-1 (Sekisui Chemical Co., Ltd.)
Polyvinylacetal diethylamino acetate: AEA (Mitsubishi-Kagaku Foods Corporation)

TABLE 4

Cosmetic milky lotion A

| Component | (%) |
|---|---|
| Purified water | 74 |
| Methylpolysiloxane | 5 |
| Ethyl p-hydroxybenzoate | 0.1 |
| Methyl p-hydroxybenzoate | 0.4 |
| 1,3-butylene glycol | 0.5 |
| Glycerin | 10 |
| Vaseline | 0.5 |
| Carboxyvinyl polymer | 0.2 |
| Neopentyl glycol dicaprate | 3.5 |
| Stearyl alcohol | 0.4 |
| Cetanol | 0.6 |
| Sodium N-stearoyl-N-methyltaurine | 0.5 |
| Sodium polyoxyethylenelaurylpetherphosphate | 0.3 |
| Sorbitan monostearate | 0.2 |
| Polyoxyethylenesorbitan monostearate | 0.2 |
| Ceramide | 1 |
| Plant extract | 1.5 |
| pH adjusting agent | 0.1 |
| Flavoring agent | 1 |
| Total | 100 |

As is clear from the results shown in Tables 2 and 3, it is found that the coatings formed with the methods of the examples have improved effects of preventing color transfer of make-up cosmetics than those of the coatings formed with the methods of the comparative examples.

Test 2-1

The effect of preventing color transfer was evaluated as in the above-described test, except that the liquid agent and the application amount thereof were changed as shown in Table 5. The spray composition used was as in Example 1.

TABLE 5

| Liquid agent | 1 | 2 | 3 | 4 | 5 | 6 | 7 | 8 |
|---|---|---|---|---|---|---|---|---|
| Squalane | 10 | | | | | | | |
| Dimethyl silicone oil | 3 | 13 | 3 | 3 | 3 | | | |
| Light isoparaffin | | | 10 | | | | | |
| Neopentyl glycol dicaprate | | | | 10 | 30 | | | |
| Jojoba oil | | | | | | 100 | | |
| Polyethylene glycol | | | | | | | 10 | |
| 1,3-Butylene glycol | | | | | | | | 10 |
| Phenoxyethanol | 0.35 | 0.35 | 0.35 | 0.35 | 0.35 | | | |
| Acrylates/C10-30 alkyl acrylate crosspolymer | 0.3 | 0.3 | 0.3 | 0.3 | 0.3 | | | |
| 48% KOH aqueous solution | 0.07 | 0.07 | 0.07 | 0.07 | 0.07 | | | |
| EDTA•2Na | 0.01 | 0.01 | 0.01 | 0.01 | 0.01 | | | |
| Polyoxyethylene (20) 2-hexyldecyl ether | | | | | 0.4 | | | |
| Purified water | Remaining | Remaining | Remaining | Remaining | Remaining | | Remaining | Remaining |
| Total | 100 | 100 | 100 | 100 | 100 | 100 | 100 | 100 |

[Test 2-1]

| | | | | | | | | |
|---|---|---|---|---|---|---|---|---|
| Total amount of liquid agent applied (mg) | 88 | 60 | 62 | 54 | 51 | 37 | 80 | 99 |
| Basis weight of liquid agent (g/m²) | 44.8 | 30.6 | 31.6 | 27.5 | 26 | 18.8 | 40.7 | 50.4 |

TABLE 5-continued

| Liquid agent | 1 | 2 | 3 | 4 | 5 | 6 | 7 | 8 |
|---|---|---|---|---|---|---|---|---|
| Basis weight of liquid oil or polyol (g/m$^2$) | 5.8 | 4 | 4.1 | 3.6 | 8.6 | 18.8 | 4.1 | 5 |
| Evaluation of color transfer prevention | 4 | 4 | 4 | 4 | 4 | 4 | 4 | 4 |
| [Test 2-2] | | | | | | | | |
| Total amount of liquid agent applied (mg) | 32.0 | 25.0 | 27.0 | 17.0 | 20.0 | 25.0 | 25.0 | 25.0 |
| Basis weight of liquid agent (g/m$^2$) | 16.3 | 12.7 | 13.8 | 8.7 | 10.2 | 12.7 | 12.7 | 12.7 |
| Basis weight of liquid oil or polyol (g/m$^2$) | 2.1 | 1.7 | 1.8 | 1.1 | 3.4 | 12.7 | 1.3 | 1.3 |
| Evaluation of color transfer prevention (electrostatic spraying method 10 sec: sheet weight 2.7 mg) | 4 | 4 | 4 | 4 | 4 | 4 | 4 | 4 |
| Evaluation of color transfer prevention (electrostatic spraying method 2 sec: sheet weight 0.6 mg) | 3 | 3 | 3 | 3 | 3 | 3 | 2 | 2 |

Dimethyl silicone oil: KF-96A-6cs (kinetic viscosity 10 mm$^2$/s Shin-Etsu Chemical Co. Ltd.)
Light isoparaffin: Parleam EX (NOF Corporation)
Neopentyl glycol dicaprate: Estemol N01 (The Nisshin OilliO Group, Ltd)
Phenoxyethanol: Hisolve EPH (Toho Chemical Industry Co., Ltd.)
Acrylates/C10-30 alkyl acrylate crosspolymer: Pemulen TR-2 (Lubrizol Advanced Materials)
EDTA•2Na: Clewat N (Nagase ChemteX Corporation)
Polyoxyethylene (20) 2-hexyldecyl ether: Emulgen 1620 (Kao Corporation)

As is clear from the results shown in Table 5, it is found that the effects of preventing color transfer of make-up cosmetics are high even when the types of oils or polyols used in the liquid agent are changed.

Test 2-2

As in Test 2-1, the liquid agent and the application amount thereof were changed as shown in Table 5, and the effect of preventing color transfer was evaluated as in the above-described tests. In this test, the effects of preventing color transfer were evaluated in cases where the electrostatic spraying was performed for 10 seconds and for 2 seconds.

As is clear from the results shown in Table 5, it is found that the effects of preventing color transfer of make-up cosmetics are high even when the types of oils or polyols used in the liquid agent are changed. Furthermore, it is found that the methods using a liquid agent containing an oil realizes improved effects of preventing color transfer of make-up cosmetics than those of the methods using a liquid agent containing no oil.

INDUSTRIAL APPLICABILITY

According to the present invention, a coating is formed on skin onto which powder-containing cosmetics have been applied, and thus color transfer and sticking of the cosmetics to clothes or the like are effectively prevented. Accordingly, the powder-containing cosmetics are stably kept on the skin.

The invention claimed is:

1. A coating formation method, comprising electrostatically spraying a composition directly onto a skin surface onto which a powder-containing cosmetic has been applied, thereby forming a coating comprising a deposit of continuous fibers on the skin,
   wherein the composition consists of a component (a), a component (b), and optionally a component (c):
   (a) 50 mass % or more of one or more volatile substances selected from the group consisting of ethanol, 1-butanol, and mixtures thereof; and
   (b) 4 mass % to 45 mass % of one or more water-insoluble polymers having a coating formation ability selected from the group consisting of polyvinylacetal diethylamino acetate and polyvinyl butyral; and
   (c) optionally one or more components selected from the group consisting of a plasticizer fix the polymer having a coating formation ability to be used as the component (b), a coloring pigment, an extender pigment, a dye, a surfactant, a UV protection agent, a flavoring agent, a repellent, an antioxidant, a stabilizer, an antiseptic, and a various vitamin,
   wherein said composition has a viscosity of 50 mPa·s to 1500 mPa·s, at 25° C., and
   wherein said continuous fibers have a length which is at least 100 times greater than their thickness, and
   wherein said fibers have a thickness of 10 nm to 3,000 nm, and
   wherein said continuous fibers are formed from said water-insoluble polymer during said electrostatic spraying of said composition, and
   wherein said method further comprises applying a liquid agent comprising one or more members selected from the group consisting of water, a polyol, an oil that is in liquid form at 20° C., and mixtures thereof on the skin onto which the cosmetic has been applied,
   wherein said applying said liquid agent is performed subsequent to said electrostatic spraying.

2. The coating formation method according to claim 1, wherein, in the electrostatic spraying, a porous coating comprising a deposit of fibers is formed, and
   in the subsequent applying, a liquid agent holding coating in which the liquid agent is present between the fibers included in the porous coating and/or on surfaces of the fibers is formed by applying the liquid agent onto the porous coating formed on the skin onto which the powder-containing cosmetics have been applied.

3. The coating formation method according to claim 1, wherein, in the applying, the transparency of the coating is maintained by applying the liquid agent onto the coating formed on the skin onto which the powder-containing cosmetics have been applied.

4. The coating formation method according to claim 1, wherein in the electrostatic spraying, the composition is electrostatically sprayed onto the skin to form a porous coating.

5. The coating formation method according to claim 1, wherein, in the electrostatic spraying, an electrostatic spraying apparatus is used to electrostatically spray the composition onto the skin to form a porous coating comprising a deposit of fibers, and
   the electrostatic spraying apparatus includes:
   a container in which the composition is accommodated;
   a nozzle from which the composition is discharged;

a supply device that supplies the composition accommodated in the container to the nozzle; and a power source that applies a voltage to the nozzle.

6. The coating formation method according to claim 1, wherein said component (b) is poly vinyl butyral.

7. A coating formation method, comprising electrostatically spraying a composition directly onto a skin surface onto which a powder-containing cosmetic has been applied, thereby forming a coating comprising a deposit of continuous fibers on the skin, wherein the composition consists of a component (a), a component (b), and optionally a component (c):

(a) 50 mass % or more of one or more volatile substances selected from the group consisting of ethanol, 1-butanol, and mixtures thereof; and (b) 4 mass % to 45 mass % of one or more water-insoluble polymers having a coating formation ability selected from the group consisting of polyvinylacetal diethylamino acetate and polyvinyl butyral; and (c) optionally one or more components selected from the group consisting of a plasticizer for the polymer having a coating formation ability to be used as the component (b), a coloring pigment, an extender pigment, a dye, a surfactant, a UV protection agent, a flavoring agent, a repellent, an antioxidant, a stabilizer, an antiseptic, and a various vitamin, wherein said composition has a viscosity of 50 mPa·s to 1500 mPa·s, at 25° C., and wherein said continuous fibers have a length which is at least 100 times greater than their thickness, and wherein said cosmetic is a make-up cosmetic that comprises an oil which is in liquid form at 25° C.

8. A coating formation method, comprising:

(i) applying a powder-containing cosmetic to a skin surface;

(ii) applying a liquid agent comprising one or more members selected from the group consisting of water, a polyol, an oil that is in liquid form at 20° C., and mixtures thereof on said skin onto which said cosmetic has been applied; and (iii) electrostatically spraying a composition directly onto said skin surface onto which said liquid agent has been applied, thereby forming a coating comprising a deposit of continuous fibers on said skin, wherein said composition consists of a component (a), a component (b), and optionally a component (c):

(a) 50 mass % or more of one or more volatile substances selected from the group consisting of ethanol, 1-butanol, and mixtures thereof; and (b) 4 mass % to 45 mass % of one or more water-insoluble polymers having a coating formation ability selected from the group consisting of polyvinylacetal diethylamino acetate and polyvinyl butyral; and (c) optionally one or more components selected from the group consisting of a plasticizer for the polymer having a coating formation ability to be used as the component (b), a coloring pigment, an extender pigment, a dye, a surfactant, a UV protection agent, a flavoring agent, a repellent, an antioxidant, a stabilizer, an antiseptic, and a various vitamin, wherein said composition has a viscosity of 50 mPa·s to 1500 mPa·s, at 25° C., and wherein said continuous fibers have a length which is at least 100 times greater than their thickness, and wherein said continuous fibers have a thickness of 10 nm to 3,000 nm, and wherein said continuous fibers are formed from said water-insoluble polymer during said electrostatic spraying of said composition.

* * * * *